US008554035B2

(12) United States Patent
Xu et al.

(10) Patent No.: US 8,554,035 B2
(45) Date of Patent: Oct. 8, 2013

(54) PRODUCTION OF OPTICAL PULSES AT A DESIRED WAVELENGTH USING SOLITON SELF-FREQUENCY SHIFT IN HIGHER-ORDER-MODE FIBER

(75) Inventors: Chris Xu, Ithaca, NY (US); James Van Howe, Cortland, NY (US); Jennifer Lee, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 246 days.

(21) Appl. No.: 12/446,619
(22) PCT Filed: Oct. 26, 2007
(86) PCT No.: PCT/US2007/082625
§ 371 (c)(1), (2), (4) Date: Dec. 7, 2009
(87) PCT Pub. No.: WO2008/052155
PCT Pub. Date: May 2, 2008

(65) Prior Publication Data
US 2010/0086251 A1 Apr. 8, 2010

Related U.S. Application Data

(60) Provisional application No. 60/863,082, filed on Oct. 26, 2006, provisional application No. 60/896,357, filed on Mar. 22, 2007.

(51) Int. Cl.
| G02B 6/00 | (2006.01) |
| G02B 6/26 | (2006.01) |
| G02B 6/42 | (2006.01) |
| H01S 3/30 | (2006.01) |
| H01S 3/10 | (2006.01) |
| G02F 1/35 | (2006.01) |
| G02F 2/02 | (2006.01) |

(52) U.S. Cl.
USPC .............. 385/122; 385/28; 372/6; 372/21; 372/23; 372/25; 359/327

(58) Field of Classification Search
USPC ............... 385/28, 122; 372/6, 20, 21, 23, 372/25; 359/326, 327
See application file for complete search history.

(56) References Cited

U.S. PATENT DOCUMENTS 6,014,249 A * 1/2000 Fermann et al. ........... 359/341.1
6,134,372 A 10/2000 Ichikawa et al.
(Continued)

OTHER PUBLICATIONS

"Soliton induced supercontinuum generation in photonic crystal fiber" by Sakamaki et al, IEEE Journal of Selected Topics in Quantum Electronics, vol. 10, No. 5, pp. 876-884, 2004.*

(Continued)

*Primary Examiner* — Ryan Lepisto
*Assistant Examiner* — Robert Tavlykaev
(74) *Attorney, Agent, or Firm* — William Greener; Bond, Schoeneck & King, PLLC

(57) ABSTRACT

The present invention relates to an apparatus for producing optical pulses of a desired wavelength. The apparatus includes an optical pulse source operable to generate input optical pulses at a first wavelength. The apparatus further includes a higher-order-mode (HOM) fiber module operable to receive the input optical pulses at the first wavelength, and thereafter to produce output optical pulses at the desired wavelength by soliton self-frequency shift (SSFS). The present invention also relates to a method of producing optical pulses having a desired wavelength. This method includes generating input optical pulses using an optical pulse source, where the input optical pulses have a first wavelength and a first spatial mode. The input optical pulses are delivered into an HOM fiber module to alter the wavelength of the input optical pulses from the first wavelength to a desired wavelength by soliton self-frequency shift (SSFS) within the HOM fiber module, thereby producing output optical pulses having the desired wavelength.

53 Claims, 7 Drawing Sheets

(56) References Cited

U.S. PATENT DOCUMENTS

| | | | |
|---|---|---|---|
| 6,909,729 B2 * | 6/2005 | Ibanescu et al. | 372/6 |
| 2004/0258353 A1 * | 12/2004 | Gluckstad et al. | 385/28 |
| 2005/0043636 A1 | 2/2005 | Gaeta et al. | |
| 2005/0163426 A1 | 7/2005 | Fermann et al. | |
| 2006/0039661 A1 * | 2/2006 | Ruilier et al. | 385/123 |

OTHER PUBLICATIONS

"Dispersion-tailored few-mode fibers: a versatile platform for in-fiber photonic devices," by Ramachandran, Journal of Lightwave Technology, vol. 23, No. 11, pp. 3426-3443, Nov. 2005.*

"Femtosecond soliton pulse delivery at 800 nm wavelength in hollow-core photonic bandgap fibers," by Luan et al, Optics Express, vol. 12, No. 5, pp. 835-840, 2004.*

"Observation of soliton self-frequency shift in photonic crystal fibre," by Cormack et al, Electronics Letters, vol. 38, No. 4, pp. 167-169, 2002.*

"Soliton self-frequency shift cancellation in photonic crystal fibers," by Skryabin et al, Science, vol. 301, pp. 1705-1708, 2003.*

"Nonlinear generation of very high-order UV modes in microstructured fibers," by Efimov et al, Optics Express, vol. 11, No. 8, pp. 910-918, 2003.*

"Cherenkov radiation emitted by solitons in optical fibers," by Akhmediev et al, Physical Review A, vol. 51, No. 3, pp. 2602-2607, 1995.*

* cited by examiner

PRODUCTION OF OPTICAL PULSES AT A DESIRED WAVELENGTH USING SOLITON SELF-FREQUENCY SHIFT IN HIGHER-ORDER-MODE FIBER

RELATED APPLICATION

This application claims benefit of U.S. Provisional Application No. 60/896,357 filed Mar. 22, 2007 and U.S. Provisional Application No. 60/863,082 filed Oct. 26, 2006 which are hereby incorporated by reference.

FIELD OF THE INVENTION

The present invention relates to the production of optical pulses at a desired wavelength using Chernekov radiation in higher-order-mode fibers.

BACKGROUND OF THE INVENTION

Higher-order-mode (HOM) fiber has attracted significant interest recently due to the freedom it provides to design unique dispersion characteristics in all-solid silica (non-holey) fibers. This new fiber platform allows for anomalous dispersion below 1300 nm by propagating light solely in one of the higher-order modes. The unique characteristics of the HOM fiber, such as large anomalous dispersion and a large effective area (approximately ten times that of PCFs), provide a number of new opportunities for applications in nonlinear fiber optics. For example, soliton self-frequency shift (SSFS) below 1300 nm could be obtained in an HOM fiber. The advantage of using HOM fiber lies in the ability to generate higher energy self-frequency shifted solitons than attainable in microstructured PCFs. Output pulse energy obtainable for cleanly frequency-shifted solitons in index-guided PCFs is limited to fractions of a nanojoule due to light confinement to a smaller effective area, rendering pulses more susceptible to nonlinearity. In contrast, the HOM fiber platform allows advantages of dispersion curves similar to PCFs, yet with a higher tolerance to nonlinearity. The ability to obtain complex dispersive profiles in fiber is advantageous because of its prospect for realizing sources in hard-to-access spectral regions by exploiting the generation of Cherenkov radiation: that is, the dispersive waves shed by solitons near the zero-dispersion wavelength. HOM fibers, with their higher tolerance to nonlinearities, will allow for energetic sources at wavelengths where sources are not currently available.

Cherenkov radiation in fibers has been demonstrated in microstructured fibers pumped near the zero-dispersion wavelength as well as experiments generating self-frequency shifted solitons. An ideal soliton requires a perfect balance between dispersion and nonlinearity so that energy becomes confined to a discrete packet both spectrally and temporally. With the introduction of perturbations such as higher-order dispersion, this stable solution breaks down, allowing the transfer of energy between the soliton in the anomalous dispersion regime and newly shed dispersive radiation in the normal dispersion regime. Such energy transfer occurs most efficiently in fibers for solitons near the zero-dispersion wavelength. The spectral regime to which energy couples most efficiently has been dubbed "Cherenkov radiation" due to an analogous phase matching condition in particle physics. The phenomenon of Cherenkov radiation in fibers is often associated with soliton self-frequency shift as it allows a convenient mechanism for more efficient energy transfer between the soliton and the Cherenkov band. When the third-order dispersion is negative, soliton self-frequency shift will shift the center frequency of the soliton toward the zero-dispersion wavelength, resulting in efficient energy transfer into the Cherenkov radiation in the normal dispersion regime. A more rigorous description and analytical derivation of Cherenkov radiation in fibers can be found in various theoretical works.

Although Cherenkov radiation can be used in wavelength conversion, the pulse energy is too low for a variety of practical applications. Thus, it would be desirable to use an NOM fiber to produce a fixed output frequency by exciting Cherenkov radiation. This invention is directed to overcoming these and other deficiencies in the art.

SUMMARY OF THE INVENTION

An example apparatus for producing optical pulses of a desired wavelength is disclosed. The apparatus includes an optical pulse source operable to generate input optical pulses at a first wavelength. A higher-order-mode (HOM) fiber module is operable to receive the input optical pulses at the first wavelength. The fiber produces output optical pulses at the desired wavelength by exciting Cherenkov radiation.

Another example is a method of producing optical pulses having a desired wavelength. Input optical pulses are generated using an optical pulse source. The input optical pulses have a first wavelength and a first spatial mode. Cherenkov radiation is excited using the generated input optical pulses. The input optical pulses are delivered into a higher-order-mode (HOM) fiber module to alter the wavelength of the input optical pulses from the first wavelength to a desired wavelength using the excited Cherenkov radiation within the HOM fiber module, thereby producing output optical pulses having the desired wavelength.

Additional aspects will be apparent to those of ordinary skill in the art in view of the detailed description of various embodiments, which is made with reference to the drawings, a brief description of which is provided below.

Figure 1:
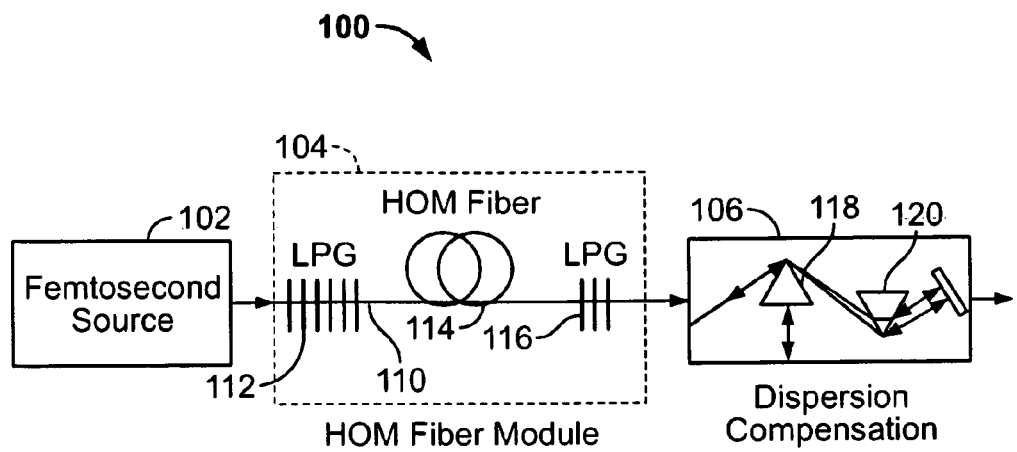
FIG. 1 is a block diagram of a higher-order-mode (HOM) fiber system that produces optical pulses at a desired wavelength using Chernekov radiation.

While these examples are susceptible of embodiment in many different forms, there is shown in the drawings and will herein be described in detail preferred examples with the understanding that the present disclosure is to be considered as an exemplification and is not intended to limit the broad aspect to the embodiments illustrated.

DETAILED DESCRIPTION

FIG. 1 shows an example HOM fiber based system 100. The example HOM fiber based system 100 includes an optical pulsed source 102, an HOM fiber module 104 and a dispersion compensation module 106.

In FIG. 1, the example pulsed source 102 includes a pulsed fiber laser (Fianium FP 1060-1 S) centered at 1064 nm, with a 80 MHz repetition rate and a subpicosecond pulse width such as a 200 fs pulse width. The output of the pulsed source 102 produces the optical pulses at the 1064 nm wavelength in this example to excite solitons and wavelength shifted solitons. In this example, the optical pulse source 102 may generate pulses having a pulse energy between about 1.0 nJ and 100 nJ. The pulse source 102 may be a mode locked fiber laser or a chirped pulse amplification system. In general, the pulse source is ideally within the transparent region of a silica based fiber having a silica based fiber having a wavelength between 300 nm and 1300 nm.

In this example, the HOM fiber module 104 includes a 12.5 cm standard single mode fiber (flexcore) pigtail 110, 2.5 cm of a long period grating (LPG) 112 and 1 m of HOM fiber 114. The HOM fiber 114 may produce output optical pulses such that a desired wavelength is a wavelength within the transparent region of a silica based fiber. The LPG 112 in this example is a mode converter that converts the fundamental mode to the higher-order $LP_{02}$ mode with good (>90%) efficiency over a large (50 nm in this example) bandwidth. For the input wavelength of 1064 nm, 99% of the fundamental mode is converted to the $LP_{02}$ mode. The output of the HOM fiber 114 is coupled to another optional LPG 116. The dispersion compensation module 106 includes a pair of silicon prisms 118 and 120.

Figure 2A:
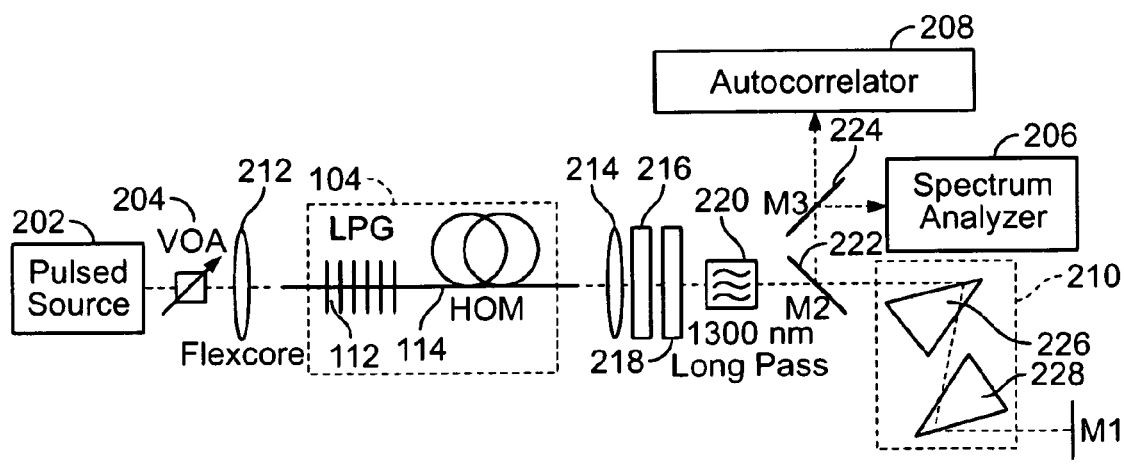
FIG. 2A is a block diagram of a measurement system used to couple light through a higher-order mode fiber module shown in FIG. 1.

FIG. 2A shows an example system 200 for the HOM fiber module 104 of the HOM fiber based system 100 in FIG. 1. The system 200 in FIG. 2A includes a pulsed source 202 similar to the pulsed source 102 from FIG. 1, a variable optical attenuator (VOA) 204 and a modified version of the HOM fiber module 104 in FIG. 1. An optical spectrum analyzer 206 and a second order interferometric autocorrelator 208 measure the output of the HOM fiber module 104 after a dispersion compensation module 210 (similar to the dispersion compensation module 106 in FIG. 1). The output of the pulsed source 202 is attenuated through the VOA 204 and focused through a collimating lens 212. The modified HOM fiber module 104 includes the single mode fiber 110 and LPG 112. The output from the HOM fiber 114 is coupled through a focusing lens 214 and a quarter wave plate 216 and a half wave plate 218.

The output of the HOM fiber module 104 is filtered via a long pass filter 220 in this example. The signal is then propagated through the dispersion compensation module 210 and then directed to the optical spectrum analyzer 206 and autocorrelator 208 using a mirror 222. Another mirror 224 splits the signal between the autocorrelator 208 and the spectrum analyzer 206. The dispersion compensation module 206 includes two prisms 226 and 228 for performing dispersion compensation.

Figure 2B:
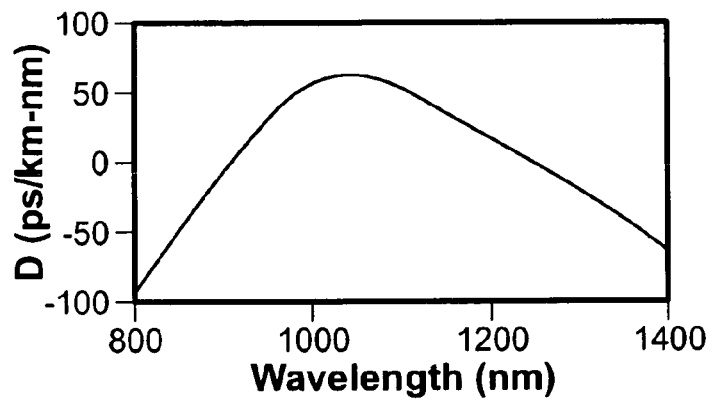
FIG. 2B is a graph of the total dispersion for propagation in the $LP_{02}$ mode as determined by the system in FIG. 2A.
Figure 2C:
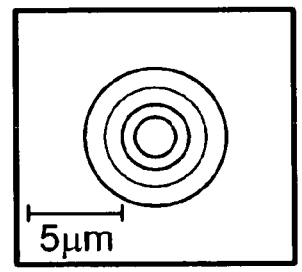
FIG. 2C is a near-field image of the $LP_{02}$ mode with effective area Aeff=44 $\mu m^2$ as determined by the system in FIG. 2A.

FIG. 2B shows a graph of the measured dispersion for the LP02 mode in the HOM fiber 114 of the HOM module 104 measured in the system 200 in FIG. 2A. The HOM fiber 114 exhibits anomalous dispersion and negative dispersion slope characteristics between approximately 1030 and 1247 nm as shown in FIG. 2B. FIG. 2C shows the measured mode profile of the LP02 mode. At the input wavelength, the $LP_{02}$ mode, shown in FIG. 2C, has an effective area $A_{eff}$=44 μm².

In the system 200, the output of the HOM fiber module 104 is collimated and measured with the optical spectrum analyzer 206 and the second order interferometric autocorrelator 208. The 1300 nm long-pass filter 220 is used to select out the Cherenkov radiation. In addition to dispersion compensation, the pair of silicon prisms 226 and 228 are used to simultaneously filter out any residual pump wavelength. A polarizer and a half-wave plate serve as the variable optical attenuator (VOA) 204 at the input of the HOM fiber module 104.

The HOM fiber module 104 in the system 100 in FIG. 1 therefore allows the generation of Cherenkov radiation at 1350 nm in the HOM fiber with 20% power conversion efficiency (approximately 25% photon efficiency). The Cherenkov output pulses are filtered and compressed to 106 fs. Cherenkov radiation generated in the normal dispersion regime of the example HUM fiber may be used to create a three-color femtosecond source (centered at the pump, frequency shifted soliton, and Cherenkov radiation wavelengths). This example HOM fiber 114 may be used to generate femtosecond pulses at various wavelengths in the energy regime of several nJs.

Figure 3A:
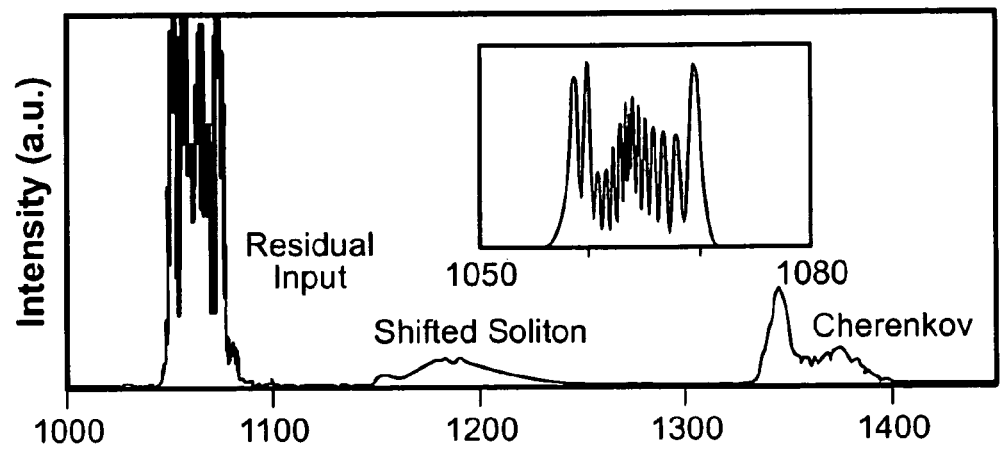
FIG. 3A is a graph of the optical spectrum at the output of the HOM fiber system of FIG. 1 obtained from experiment.
Figure 3B:
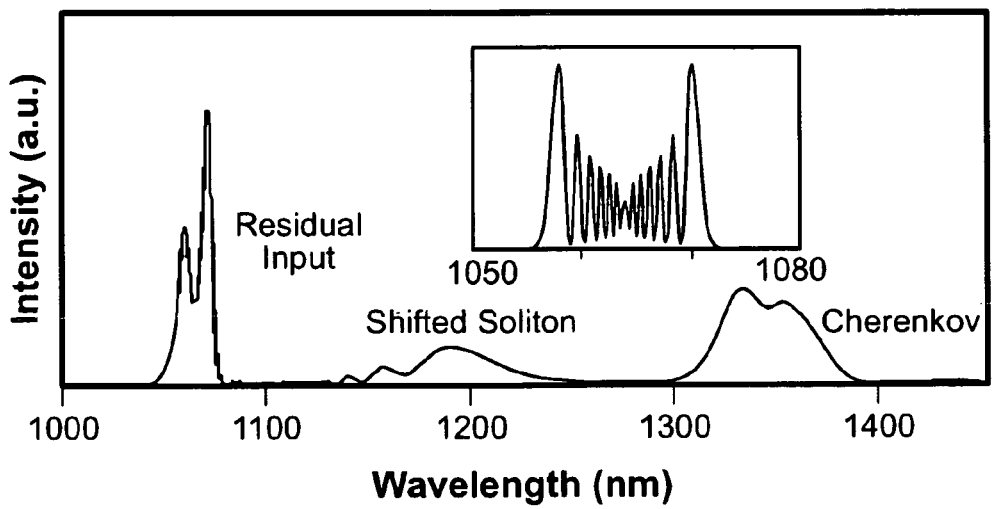
FIG. 3B is a graph of the optical spectrum at the output of the HOM fiber system of FIG. 1 obtained from numerical simulation.

FIG. 3A is a graph of the optical spectrum at the output of the HOM fiber system of FIG. 1 obtained from experiment while FIG. 3B is a graph of the optical spectrum at the output of the HOM fiber system 100 of FIG. 1 obtained from numerical simulation. The system 100 in FIG. 1 is numerically simulated using a standard split-step Fourier method. The source is modeled as a Gaussian pulse with added self-phase modulation (SPM) to approximately match the source spectrum from the measurement system 200 in FIG. 2A as shown in the graphs in FIGS. 3A and 3B. For propagation in the HOM fiber 114, a nonlinear parameter $\gamma$=2.2 $W^{-1}$ $km^{-1}$), stimulated Raman scattering (Raman response $T_R$=5 fs), self-steepening, wavelength dependent $A_{eff}$, and dispersion up to fifth-order is included in this example. Dispersion coefficients are calculated by numerically fitting the dispersion curve shown in FIG. 3B. The power is scaled accordingly during Raman wavelength-shifting to take into account energy lost to phonons.

In this example, a total power of 265 mW (3.31 nJ pulse energy) is coupled into the HOM fiber module 104 in FIG. 2A. At this power level, the residual input, shifted soliton, and Cherenkov radiation may be clearly seen in the output spectrum shown in FIG. 3A. The optical power residing in the Cherenkov band is approximately 53 mW (0.66 nJ pulse energy) and has a power conversion efficiency of 20% (25% photon conversion efficiency). The experimental spectrum is qualitatively matched in the simulation as shown in FIG. 3C.

An excellent qualitative match is achieved between simulation and experiment and a relatively good quantitative match is achieved.

This simulated spectrum corresponds to an input power of 189 mW (2.36 nJ pulse energy), with 30% conversion to the Cherenkov band, equivalently 0.70 nJ in the Cherenkov pulse. At this power level, the soliton (centered at approximately 1200 nm) has shifted enough energy past the zero-dispersion wavelength so that resonant coupling occurs efficiently at 1350 nm (Cherenkov radiation). Intuitively, growth of the Cherenkov radiation begins exponentially with increasing input power until the "spectral recoil" exerted by the Cherenkov radiation on the soliton cancels the Raman self-frequency shift. After the soliton is frequency-locked, in this example, at 1200 nm, increasing the pump power will only transfer energy to the Cherenkov spectrum instead of shifting the soliton further. The simulation shows that up to approximately 5 nJ can be pumped into the Cherenkov band, after which nonlinear effects begin to degrade the system.

Figure 4:
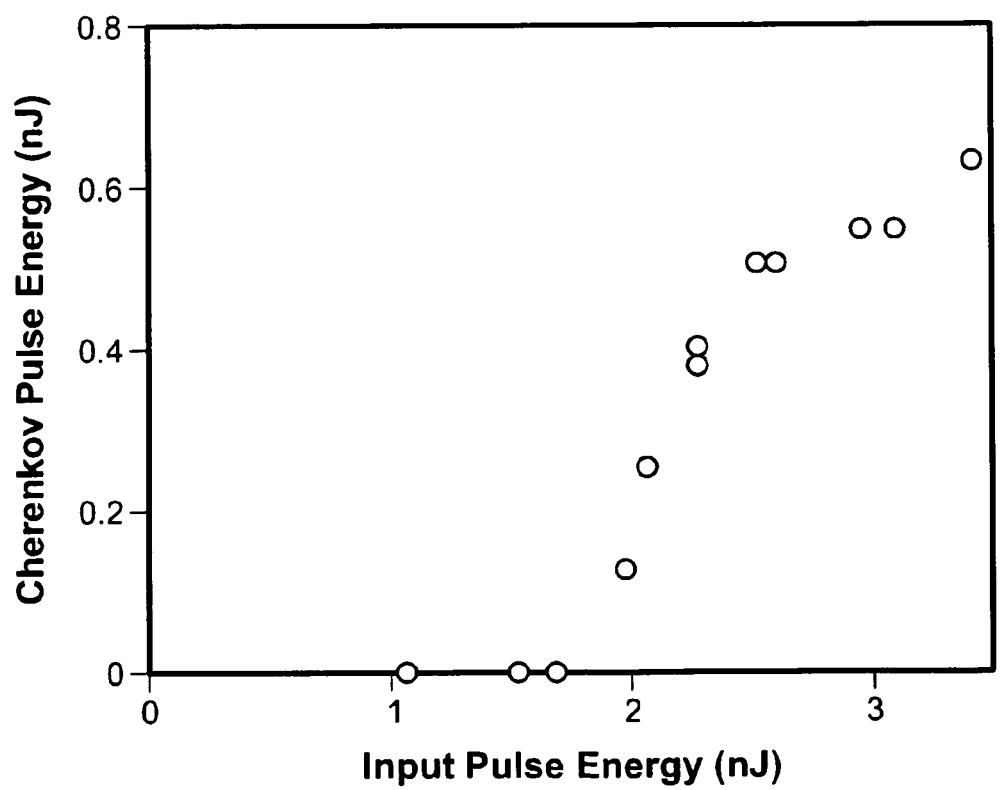
FIG. 4 is a plot of Cherenkov output pulse energy as a function of input pulse energy of the HOM fiber system of FIG. 1.

Cherenkov output pulse energy is also measured as a function of input pulse energy by varying the attenuation at the input of the HOM fiber module 104 in FIG. 1. FIG. 4 is a plot of Cherenkov output pulse energy as a function of input pulse energy of the HOM fiber system 100 of FIG. 1. FIG. 4 shows that the Cherenkov pulse energy increases rapidly at input energies of approximately 2 nJ (input power 160 mW). This "threshold" behavior, as well as the location of the knee in FIG. 4 agrees with the simulation. The threshold behavior has also been experimentally observed previously in photonic crystal fibers. A discrepancy in Cherenkov pulse energy between numerical results and was found at the highest input pulse energies investigated, where simulation shows a faster increase in Cherenkov energy than the actual results.

Figure 5A:
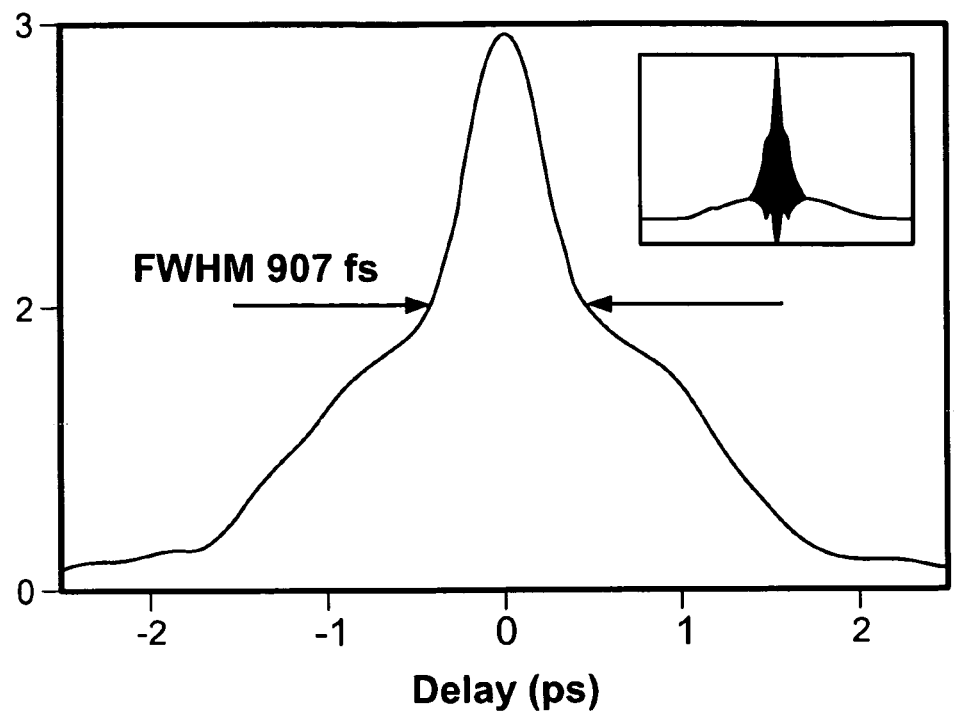
FIG. 5A shows an intensity autocorrelation trace of the Cherenkov pulse at the output of the HOM fiber module in FIG. 2A without dispersion compensation.
Figure 5B:
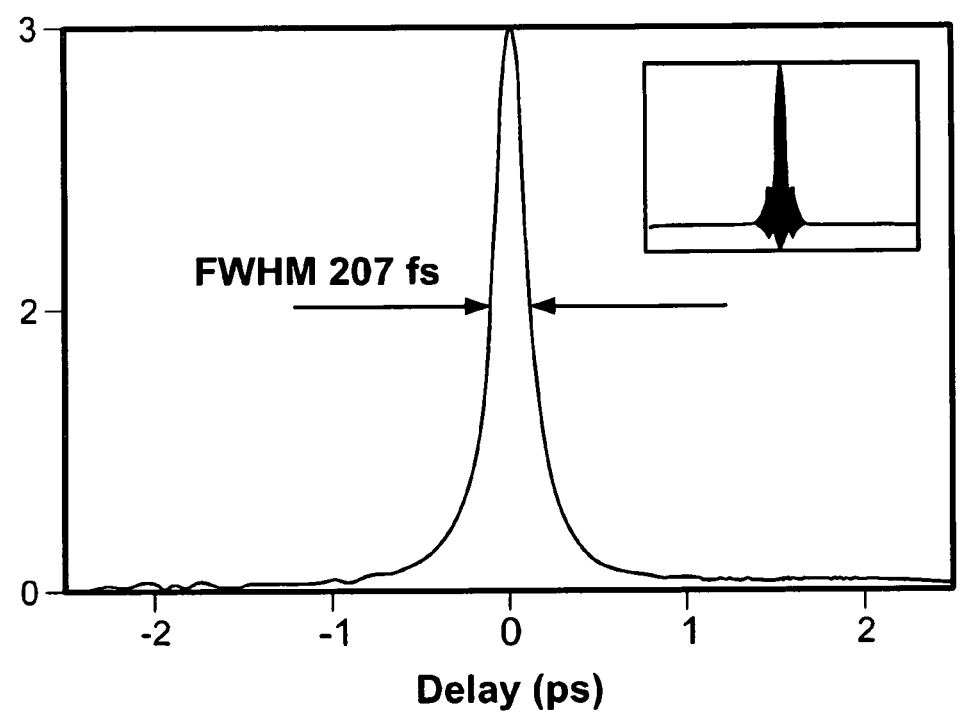
FIG. 5B shows an intensity autocorrelation trace of the Cherenkov pulse at the output of the HOM fiber module in FIG. 2A with dispersion compensation.

A second order autocorrelation trace of the filtered Cherenkov pulse without dispersion compensation at the output of the HOM fiber module 104 in FIG. 2A is shown in FIG. 5A. FIG. 5B shows an intensity autocorrelation trace of the Cherenkov pulse after dispersion compensation from the HOM fiber module 104 in FIG. 2A. The filtered Cherenkov pulse is visibly chirped and has an autocorrelation full width at half maximum of 907 fs. This pulse is compressed to 207 fs autocorrelation full width at half maximum as shown in FIG. 5B, with appropriate dispersion compensation by the pair of silicon prisms 226 and 228 in FIG. 2A. The dispersion provided by the pair of silicon prisms 226 and 228 is calculated (prism separation distance approximately 7 cm in optical pathlength) to be $\beta_2 = -0.0065$ ps$^2$ and $\beta_3 = -1.9 \times 10^{-5}$ ps$^3$ in this example. Applying such dispersion compensation values to the spectrally matched simulation, an autocorrelation full width at half maximum of 200 fs and a pulsewidth of 103 fs is numerically obtained. Assuming the same pulse shape, the experimentally measured deconvolved pulsewidths with and without dispersion compensation are 106 fs and 465 fs, in FIGS. 5B and 5A respectively.

The location of the Cherenkov radiation can be tuned through engineering of the fiber dispersion. For example, simple dimensional scaling of the index profile of the HOM fiber can be used to shift the dispersion curve of the $LP_{02}$ mode. By shifting the zero-dispersion wavelength 50 nm to the shorter wavelength side, the generated Cherenkov radiation will also shift by approximately the same amount. Such design control leads to the generation of useful femtosecond pulsed sources in spectral regimes unattainable by current laser systems. Furthermore, the large effective area and flexibility for dispersion engineering in the HOM fiber open up the possibility to achieve pulse energies significantly beyond the levels in the above examples.

As shown in FIG. 2A, the generated Cherenkov pulse can be converted back to the fundamental mode by the optional second LPG 116 at the output of the HOM fiber 114 in the HOM fiber module 104 in FIG. 1. FIG. 1 shows the HOM fiber module 104 with the second optional LPG 116 coupled to the output of the HOM fiber 104 to convert the Chernekov pulse back to the fundamental mode. It is to be understood that depending on the intended usage, the higher order mode output could also be used directly without mode conversion.

The capability to numerically predict the behavior of Cherenkov radiation in an HOM fiber such as the HOM fiber 114 in FIG. 1 allows the design of pulsed sources using Chrenkov radiation. The HOM fiber in this example converts the wavelength to 1.3 μm instead of the demonstrated 1.36 μm and the output pulse energy is increased to greater than 10 nJ. The center wavelength of the Cherenkov radiation is mostly determined by the zero dispersion wavelength and the third order dispersion. The Cherenkov energy is determined by the magnitude of $D*A_{eff}$. Thus the wavelength may be converted by wavelength shifting the dispersion curve. The increase in output pulse energy is accomplished by increasing the dispersion and for effective area, $A_{eff}$ of the HOM fiber.

Figure 6A:
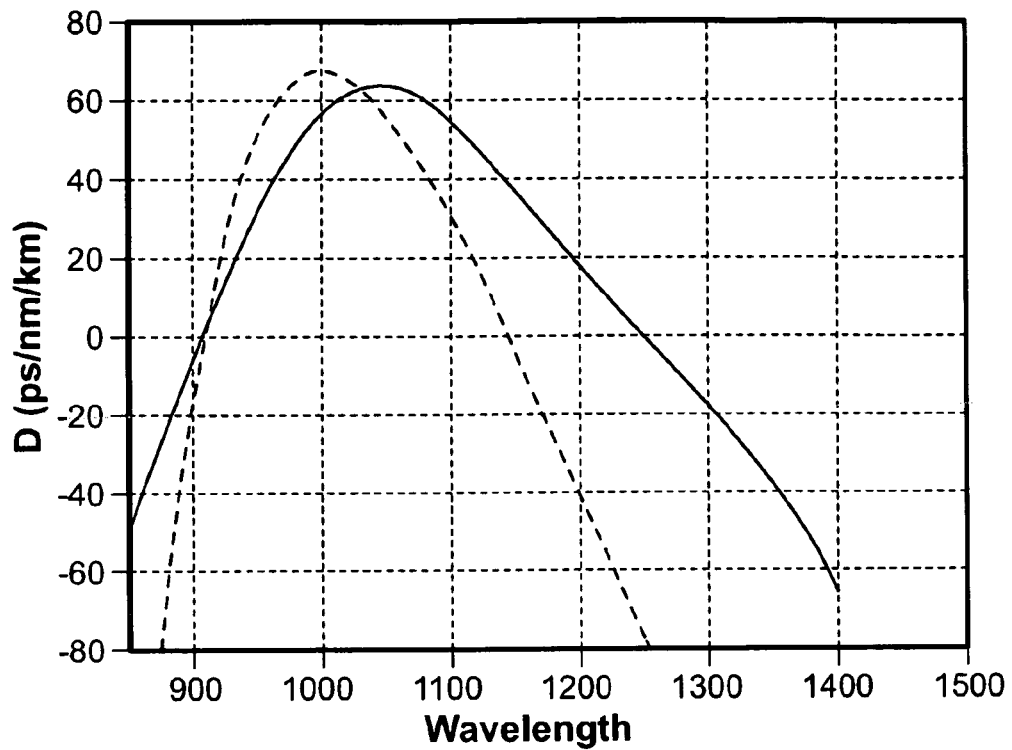
FIG. 6A is a graph of the dispersion versus wavelength for converting a 1.03 µm input pulse to a pulse at 1.27 µM via Cherenkov radiation.
Figure 6B:
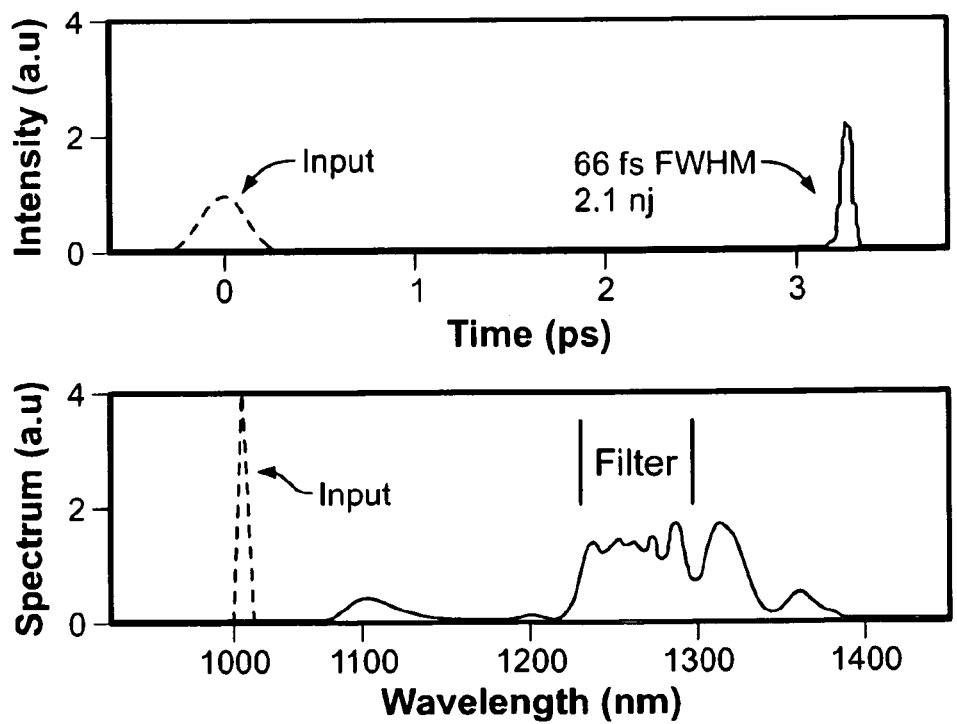
FIG. 6B is a graph of the output intensity and spectrum after propagating a pulse through an HOM fiber at a first energy.

FIG. 6A is a graph of the dispersion versus wavelength for converting 1.03 μm input pulse to a pulse at 1.27 μm via Cherenkov radiation. The dashed line in FIG. 6A is the designed dispersion while the solid line is the dispersion in an existing HOM fiber. As shown in FIG. 6A shows the required dispersion and effective area of the HOM fiber to achieve an approximately 2 nJ pulse. FIG. 6B is a graph of the output intensity (top) and spectrum (bottom) after propagating a pulse through a HOM fiber. FIG. 6B shows the numerical simulation results of the Cherenkov radiation in an HOM fiber at a 4.2 nJ input. The conversion efficiency is about 50% for a Gaussian input pulse at 280 fs width in this example. The output pulse has a width of approximately 66 fs after dispersion compensation to remove the linear chirp of the pulse. The pulse has excellent quality with more than 90% of the energy residing within the time window that is twice the full width at half maximum.

A feature of soliton Cherenkov radiation is the robustness against input variations. For example, at a 3.2 nJ input, numerical modeling predicts Cherenkov radiation at a 66 fs pulse width and 2 nJ. These results are very similar to those obtained at a 4.2 nJ input. Numerical simulations also show that fiber length variation from 25 to 45 cm essentially provide identical output characteristics except that the values for dispersion compensation need to be adjusted to achieve the shortest pulse.

Figure 7A:
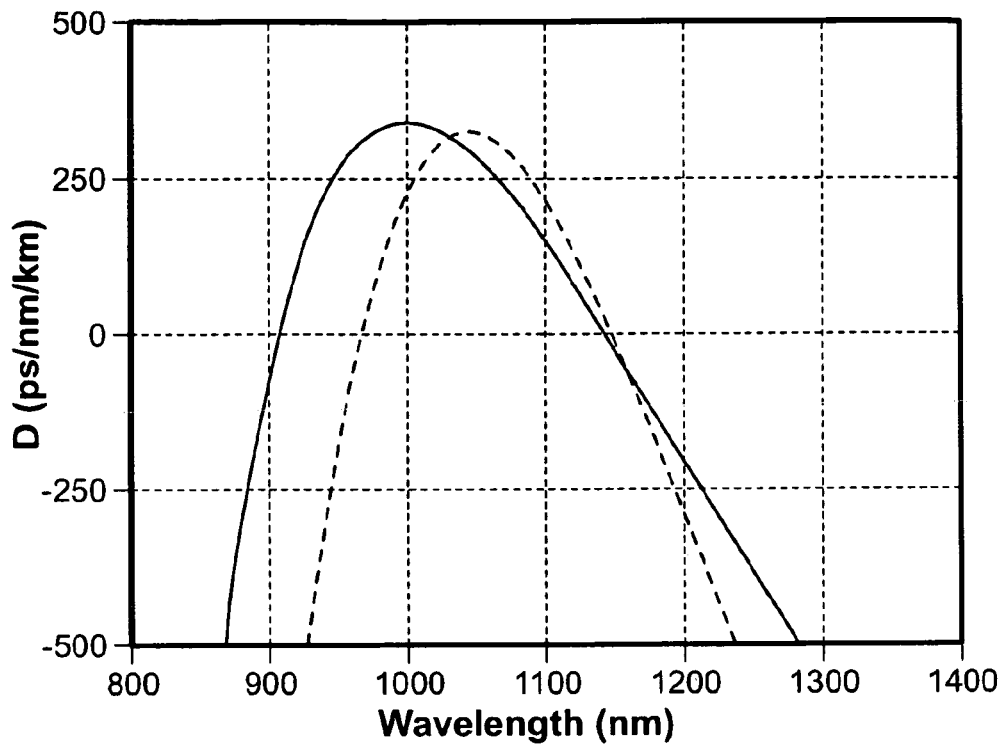
FIG. 7A is a graph of the designed dispersion versus wavelength curves for converting a 1.03 μm input pulse to a pulse at 1.27 μm via Cherenkov radiation.
Figure 7B:
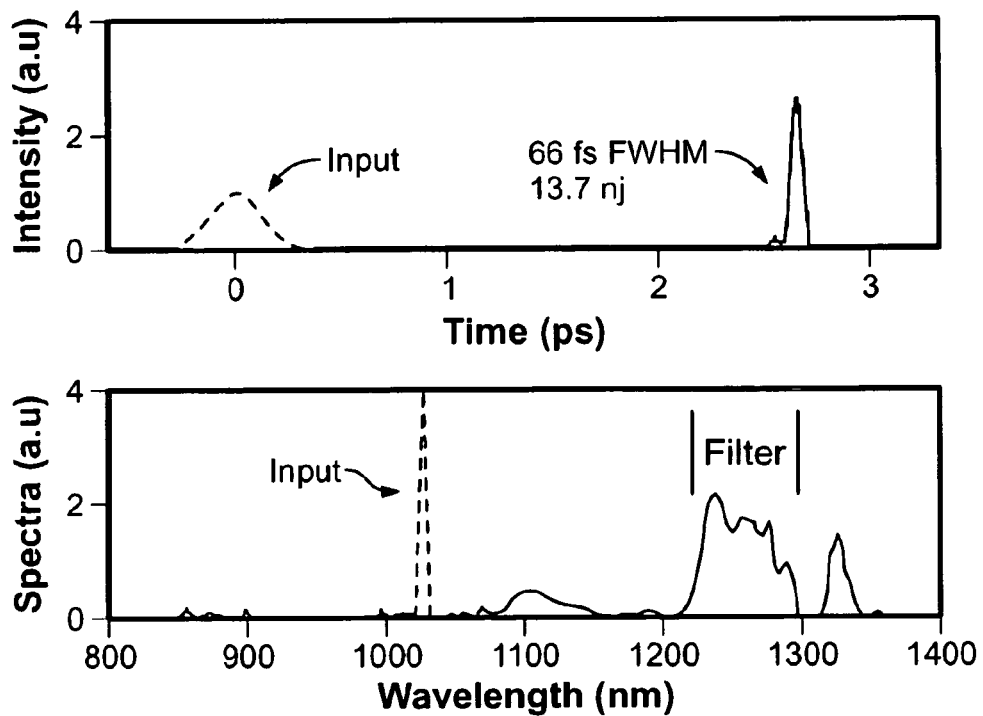
FIG. 7B is a graph of output intensity and spectrum after propagating a pulse through an HOM fiber at a different energy.

The magnitude of $D*A_{eff}$ is increased by approximately 5 times to achieve a greater than 10 nJ pulse energy. FIG. 7A is a graph of the designed dispersion versus wavelength curves for converting a 1.03 μm input pulse to a pulse at 1.27 μm via Cherenkov radiation. The results in FIG. 7A are similar to those in FIG. 6A. FIG. 7B is a graph of output intensity and spectrum after propagating a pulse through a 3 cm HOM fiber at a different 22.4 nJ energy. 13 nJ or greater Cherenkov radiation may be produced in a HOM fiber as short as 3 cm in this example. Both dispersion curves as shown in the solid and dashed lines in FIG. 7A produce similar output characteristics.

Figure 8:
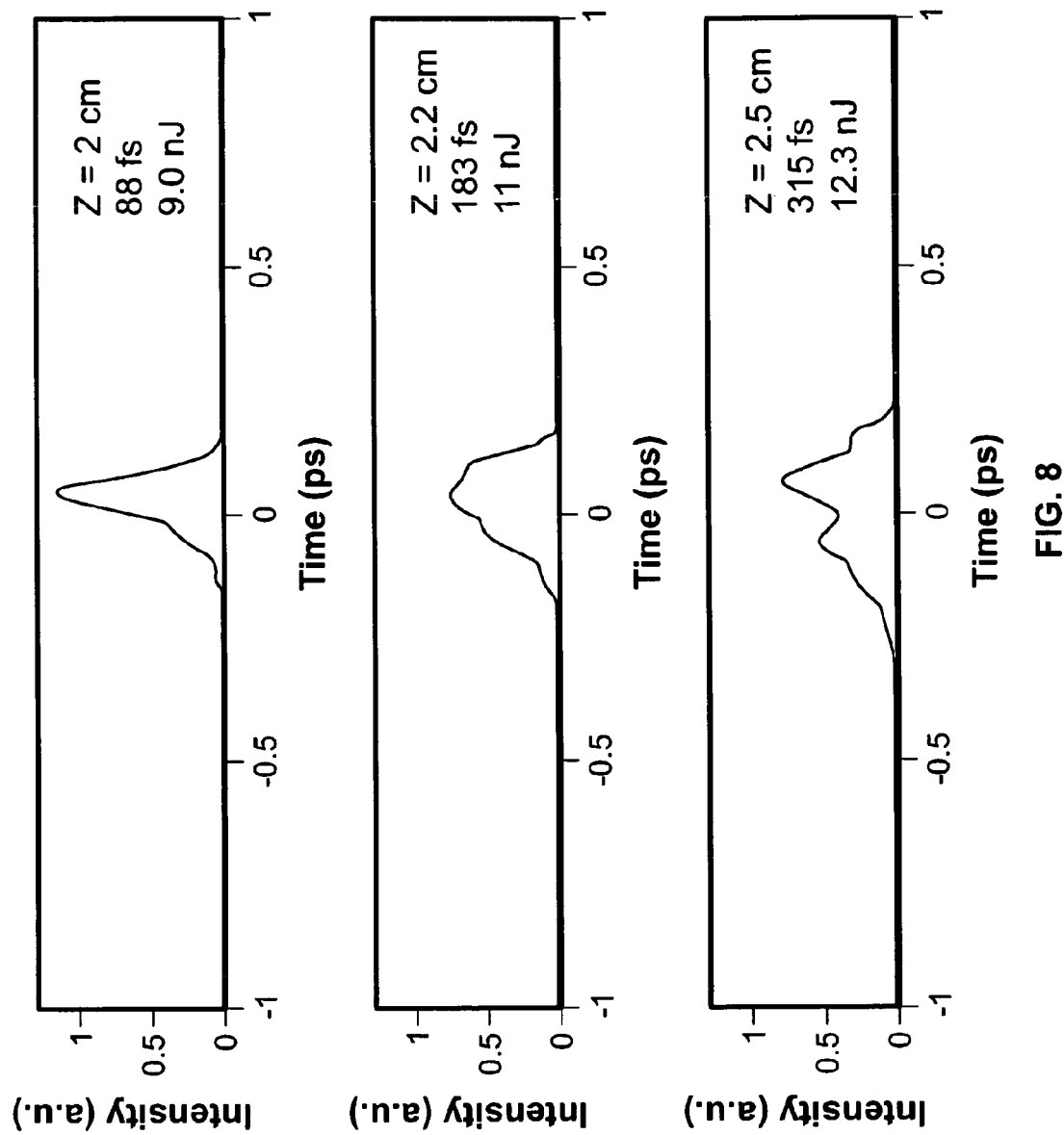
FIG. 8 is a series of output intensities plotted at various propagation distances for an input pulse energy of the HOM fiber in FIG. 1.

The short length of the HOM fiber such as the HOM fiber of FIG. 7 allows the elimination of the dispersion compensation module 106 for dispersion compensation after the HOM fiber. FIG. 8 shows the pulse width and energy directly from the HOM fiber of FIG. 7 at three propagation distances. 10 nJ pulses may be obtained at 100 to 200 fs pulse width without any dispersion compensation if the length of the HOM fiber is reduced to 2.2 cm. Although the pulse quality and energy is somewhat reduced in FIG. 8 when compared to that shown in FIG. 7A, eliminating the need for dispersion compensation is convenient and offers the opportunity for direct fiber delivery of an energetic pulse.

In summary, the system 100 in FIG. 1 allows generating short pulses at 1350 nm by exciting Cherenkov radiation in the HOM fiber 104 with a 1064 nm pulsed fiber source 102. A 465 fs pulse is dechirped at the output of the HOM fiber 114 to a 106 fs pulse with a pair of silicon prisms 118 and 120 that are in the dispersion module 106 in FIG. 1. This method of generating short pulses at 1350 nm can be extended to other wavelengths and to higher pulse energies with appropriate design of the HOM fiber 114. A power control system may be coupled between the pulsed fiber source 102 and the HOM fiber module. The power control system achieves sub-nanosecond power tuning of the output wavelength. In this example the power control system includes a lithium niobate intensity modulator device.

Certain applications may use the optical pulses produced by the HOM fiber module 104 in FIG. 1. For example, applications such as multiphoton imaging may take advantage of the HOM fiber module 104 producing output optical pulses that can penetrate animal or plant tissue at a penetration depth of at least 0.1 millimeters (mm). Other applications may include having an endoscope or optical biopsy needle terminally associated with the HOM fiber module 104 in FIG. 1. Another application may functionally associate a multiphoton microscope system or a multiphoton imaging system with the system 100 in FIG. 1.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An apparatus for producing output optical pulses of light of a desired wavelength, said apparatus comprising:
    an optical pulse source operable to generate input optical pulses at a first wavelength in a first spatial mode; and
    a higher-order-mode (HOM) fiber module including a non-photonic crystal fiber (non-PCF) HOM fiber and at least one mode converter, optically coupled to the optical pulse source to receive the input optical pulses at the first wavelength,
    wherein the light propagating in the HOM fiber module is in a non-fundamental mode that is different than the first spatial mode and has an effective area $A_{\it eff}$ that is greater than 10 microns squared ($\mu m^2$),
further wherein the output optical pulses are solitons having pulse energies between one to 10 nanoJoules (nJ) at a wavelength below 1300 nanometers (nm).

2. The apparatus according to claim 1, further comprising a dispersion compensation module.

3. The apparatus according to claim 2, wherein the dispersion compensation module includes a prism pair.

4. The apparatus according to claim 1, wherein the HOM fiber includes anomalous dispersion characteristics and negative dispersion slope characteristics.

5. The apparatus according to claim 1, wherein the HOM fiber is a solid silica-based fiber.

6. The apparatus according to claim 1, wherein the at least one mode converter is connectedly disposed between the optical pulse source and the HOM fiber.

7. The apparatus according to claim 6 further comprising a second mode converter terminally connected to the HOM fiber to convert the generated pulses back to a fundamental mode.

8. The apparatus according to claim 1, wherein the mode converter is a long period grating (LPG).

9. The apparatus according to claim 1, wherein the optical pulse source generates input optical pulses having a pulse energy of at least 1.0 nanojoule (nJ).

10. The apparatus according to claim 1, wherein the optical pulse source generates input optical pulses having a pulse energy of between about 1.0 nJ and about 100 nJ.

11. The apparatus according to claim 1, wherein the optical pulse source comprises a mode-locked laser.

12. The apparatus according to claim 1, wherein the optical pulse source comprises a chirped pulse amplification (CPA) system.

13. The apparatus according to claim 11, wherein the mode-locked laser is a modelocked fiber laser.

14. The apparatus according to claim 12, wherein the CPA system is a fiber CPA system.

15. The apparatus according to claim 1, wherein the solitons have a wavelength equal to or greater than 300 nm.

16. The apparatus according to claim 1, wherein the output optical pulses of the desired wavelength are within the transparent region of a silica-based fiber.

17. The apparatus according to claim wherein the solitons have a wavelength between 775 nm to 1000 nm.

18. The apparatus according to claim 1, wherein the solitons have a wavelength between 1030 nm and 1280 nm.

19. The apparatus according to claim 1, wherein the output optical pulses have a subpicosecond pulse width.

20. The apparatus according to claim 1 further comprising a power control system connectedly disposed between the optical pulse source and the HOM fiber module.

21. The apparatus according to claim 20, wherein the power control system achieves subnanosecond power tuning of the first wavelength.

22. The apparatus according to claim 21, wherein the power control system comprises a lithium niobate intensity modulator device.

23. The apparatus according to claim 1 further comprising a single-mode fiber (SMF) connectedly disposed between the optical pulse source and the HOM fiber module.

24. The apparatus according to claim 1 further comprising an endoscope terminally associated with the HOM fiber module.

25. The apparatus according to claim 1 further comprising an optical biopsy needle terminally associated with the HOM fiber module.

26. The apparatus according to claim 1 further comprising a multiphoton microscope system functionally associated with the apparatus.

27. The apparatus according to claim 1 further comprising a multiphoton imaging system functionally associated with the apparatus.

28. A method of producing output light having a desired wavelength, said method comprising:
    generating input optical pulses of light using an optical pulse source, wherein the input light has a first wavelength and a first spatial mode;
    exciting Cherenkov radiation using the input light;
    delivering the input light into a higher-order-mode (HOM) fiber module including a non-photonic crystal fiber (non-PCF) HOM fiber and at least one mode converter;

propagating the input light in the HOM fiber module and therein converting the first spatial mode to a higher order mode having an effective area $A_{\mathit{eff}}$ that is greater than 10 microns squared ($\mu^2$); and having pulse energies between one to 10 nanoJoules (nJ) at a desired wavelength below 1300 nanometers (nm).

29. The method according to claim 28, further comprising removing a linear chirp in the output optical pulses.

30. The method according to claim 28, further comprising filtering and compressing the output optical pulses.

31. The method according to claim 28, where the optical pulse source generates input optical pulses at the first wavelength to first excite solitons and wavelength shifted solitons, and thereafter excites Cherenkov radiation to produce output optical pulses at the desired wavelength.

32. The method according to claim 28, wherein the HOM fiber is a solid silica-based fiber.

33. The method according to claim 28 further comprising:
converting the first spatial mode of the input optical pulses into a second spatial mode prior to delivering the input optical pulses into the HOM fiber to produce output optical pulses having the second spatial mode, wherein the first spatial mode and the second spatial mode are different modes.

34. The method according to claim 33 further comprising:
reconverting the second spatial mode of the output optical pulses to another spatial mode using a mode converter terminally connected to the HOM fiber.

35. The method according to claim 28, further comprising variably attenuating the input optical pulses.

36. The method according to claim 28, wherein the optical pulse source generates input optical pulses having a pulse energy of at least 1.0 nanojoule (nJ).

37. The method according to claim 28, wherein the optical pulse source comprises a mode-locked laser.

38. The method according to claim 37, wherein the mode-locked laser is a modelocked fiber laser.

39. The method according to claim 28, wherein the optical pulse source comprises a chirped pulse amplification (CPA) system.

40. The method according to claim 39, wherein the CPA system is a fiber CPA system.

41. The method according to claim 28, wherein the first wavelength is a wavelength within the transparent region of a silica-based fiber.

42. The method according to claim 41, wherein the first wavelength is below 1300 nanometers (nm).

43. The method according to claim 42, wherein the first wavelength is a wavelength between the range of about 300 nm and about 1300 nm.

44. The method according to claim 28, wherein the input optical pulses have a subpicosecond pulse width.

45. The method according to claim 28, wherein the HOM fiber module produces output optical pulses such that the desired wavelength is a wavelength within the transparent region of a silica-based fiber.

46. The method according to claim 28, wherein the desired wavelength is equal to or greater than 300 nm.

47. The method according to claim 28, wherein the HOM fiber module produces output optical pulses having a subpicosecond pulse width.

48. The method according to claim 28 further comprising:
varying the power of the input optical pulses so as to vary the desired wavelength.

49. The method according to claim 28 further comprising:
varying at least one of a zero dispersion wavelength or dispersion slope characteristics of the HOM fiber to vary the desired output wavelength.

50. The apparatus according to claim 1, wherein the non-fundamental mode is the $LP_{02}$ mode.

51. The method according to claim 28, wherein the first spatial mode is the $LP_{01}$ mode and the higher order mode is the $LP_{02}$ mode.

52. The method according to claim 46, wherein the desired wavelength is between 775 nm to 1000 nm.

53. The method according to claim 46, wherein the desired wavelength is between 1030 nm and 1280 nm.

* * * * *

UNITED STATES PATENT AND TRADEMARK OFFICE
CERTIFICATE OF CORRECTION

| | | |
|---|---|---|
| PATENT NO. | : 8,554,035 B2 | Page 1 of 1 |
| APPLICATION NO. | : 12/446619 | |
| DATED | : October 8, 2013 | |
| INVENTOR(S) | : Chris Xu, James Van Howe and Jennifer Lee | |

It is certified that error appears in the above-identified patent and that said Letters Patent is hereby corrected as shown below:

In the Claims

Column 8, claim 17, line 28, --1-- should be inserted between "claim" and "wherein." Should appear as "claim 1 wherein ..."

Signed and Sealed this
Sixteenth Day of September, 2014

Michelle K. Lee
*Deputy Director of the United States Patent and Trademark Office*